United States Patent [19]

Rossi

[11] Patent Number: 5,370,619

[45] Date of Patent: Dec. 6, 1994

[54] SINGLE-USE SAFETY SYRINGE PROVIDED WITH RETRACTILE NEEDLE AND DEVICE PREVENTING IT FROM BEING REUSED

[76] Inventor: Lucio Rossi, Via dei Cristofori 54, 00168 Rome, Italy

[21] Appl. No.: 856,968

[22] PCT Filed: Nov. 8, 1990

[86] PCT No.: PCT/IT90/00092

§ 371 Date: May 20, 1992

§ 102(e) Date: May 20, 1992

[87] PCT Pub. No.: WO91/08788

PCT Pub. Date: Jun. 27, 1991

[30] Foreign Application Priority Data

Dec. 20, 1989 [IT] Italy ................... 48680 A/89
Jun. 7, 1990 [IT] Italy ................... 48039 A/90

[51] Int. Cl.⁵ .................................. A61M 5/00
[52] U.S. Cl. ...................... 604/110; 604/194; 604/218
[58] Field of Search ............ 604/110, 187, 194, 195, 604/196, 198, 218, 240, 263; 128/919

[56] References Cited

U.S. PATENT DOCUMENTS

| 4,507,117 | 3/1985 | Vining et al. | 604/196 |
| 4,675,005 | 6/1987 | DeLuccia | 604/110 |
| 4,747,830 | 5/1988 | Gloyer et al. | 604/110 |
| 4,790,822 | 12/1988 | Haining | 604/110 |
| 4,888,002 | 12/1989 | Braginetz et al. | 604/195 |
| 4,950,241 | 8/1990 | Ranford | 604/110 |
| 4,950,251 | 8/1990 | Haining | 604/110 |
| 4,978,340 | 12/1990 | Terrill et al. | 604/195 |
| 4,986,813 | 1/1991 | Blake et al. | 604/110 |
| 5,019,043 | 5/1991 | Segui Pastor et al. | 604/110 |
| 5,019,045 | 5/1991 | Lee | 604/110 |
| 5,030,208 | 7/1991 | Novacek et al. | 604/195 |
| 5,047,016 | 9/1991 | Dolgin et al. | 604/110 |
| 5,098,402 | 3/1992 | Davis | 604/195 |
| 5,152,750 | 10/1992 | Haining | 604/195 |

FOREIGN PATENT DOCUMENTS

| 0347742 | 12/1989 | European Pat. Off. . | |
| 8910151 | 11/1989 | WIPO . | |
| 9006148 | 6/1990 | WIPO . | |
| 9112841 | 9/1991 | WIPO | 128/919 |

*Primary Examiner*—Jerome L. Kruter
*Attorney, Agent, or Firm*—Stevens, Davis, Miller & Mosher

[57] ABSTRACT

A single-use safety syringe comprising an outer cylindrical body provided with an end spout, a needle provided with a joint adapted to releasably engage the inner wall of the end spout, and a plunger provided with a fore end adapted to releasably inwardly engage the joint of the needle so as to allow the plunger to move into the syringe and engage the end spout to make the injection. The joint has an inner seat with a widening plug projecting downwardly from a base of the seat and projections extending from walls of the seat. The fore end of the plunger has a conical axial cavity open at a frontal face of the fore end and cuts along its generatrix and a groove there around. The outer dimension of the fore end corresponds to the inner dimension of the inner seat of the joint whereby when the plunger is at the end of the injection the widening plug enters the cavity and forces walls of the cavity to spread and exert radial pressure against inner walls of the joint, with the grooves of the fore end engaging projections of the joint to lock the needle and plunger together thereby preventing reuse of the needle.

4 Claims, 2 Drawing Sheets

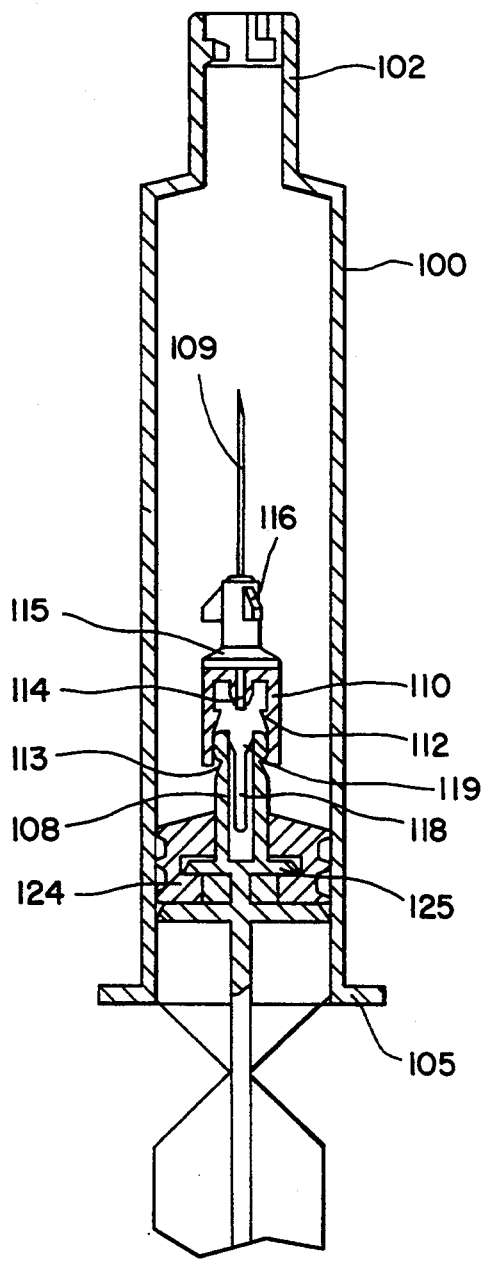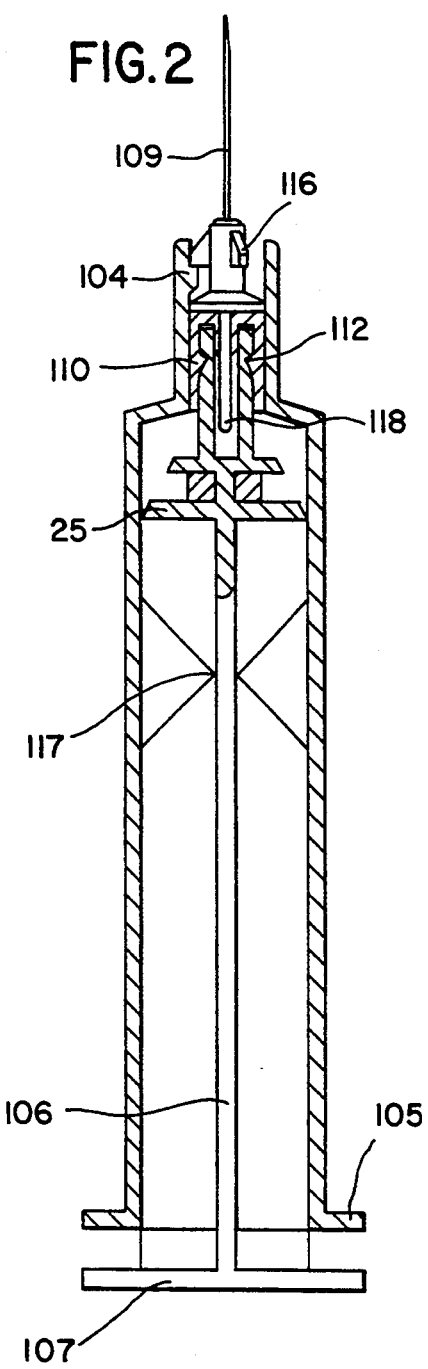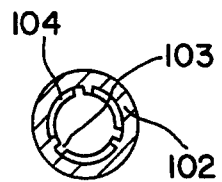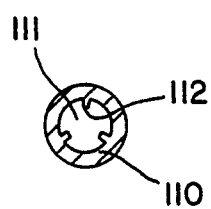

SINGLE-USE SAFETY SYRINGE PROVIDED WITH RETRACTILE NEEDLE AND DEVICE PREVENTING IT FROM BEING REUSED

BACKGROUND OF THE INVENTION

The present invention relates to a single-use syringe provided with a retractile needle and a self-locking device preventing the syringe from being filled again after the first injection.

As known it is of foremost importance to solve safety problems linked with the undue or irresponsible handling of used syringes, both for the contact risks with the used needle and for the contagious danger involved in a repeated use of the same syringe.

Recently, several syringes have been developed which show the use of retractable needles, and devices to prevent their re-use. However, the structure of these syringes is too elaborate and too expensive to manufacture.

This invention seeks to provide a solution to the above mentioned problem by means of a syringe providing ease of use, protection and inaccessibility of the needle once having made the injection.

SUMMARY OF THE INVENTION

According to the invention there is provided a syringe comprising a cylindrical body provided with a fore end, a plunger sliding in said cylindrical body, a needle receivable in said cylindrical body, said needle moving under control of the plunger from an operative position, in which it is integral with the fore end of the syringe, and projects therefrom, to a protected position where it is locked in said cylindrical body. The locking of the needle both to the body of the syringe and the plunger is made easy and reliable, and above all the syringe is prevented from being used again after the first injection.

This has been achieved by providing the base of the needle with self-engaging means which at the end of the first injection, when the plunger is at the end of its stroke, locks automatically and unreleasably the needle to the plunger and constrains it to enter the body of the syringe again if the plunger is retracted.

BRIEF DESCRIPTION OF THE DRAWING

The invention will be now described with reference to the annexed drawings showing preferred embodiments of the invention as illustrative non-limitative examples.

In the drawings:

FIG. 1 shows the syringe according to the invention with the needle releasably engaging the plunger ready to be moved to the operating position;

FIG. 2 shows the syringe after the first injection;

FIGS. 1a, 1b and 1c are sectional views respectively of the needle base, of the end spout and of the syringe's fore end;

DESCRIPTION OF THE PREFERRED EMBODIMENTS

Figure 4:
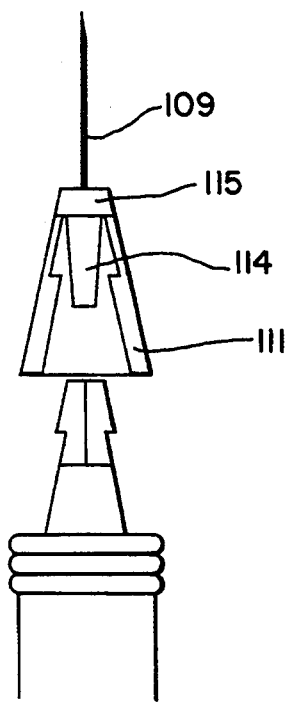
FIG. 4 shows a different embodiment of the device preventing the syringe from being re-used.
Figure 5:
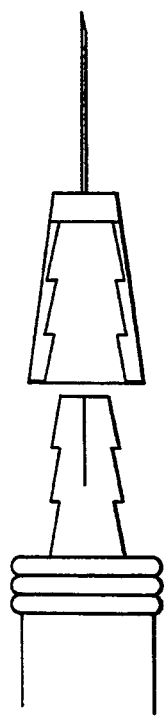
Figure 6:
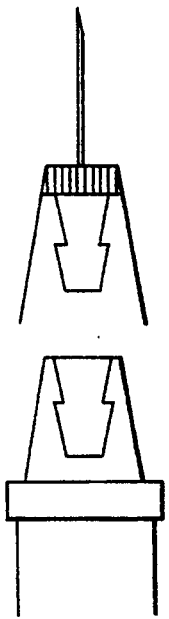

With reference to FIG. 1 numeral 100 designates a body of a syringe of proper size and suitable material which is provided with a fore end or cylindrical spout 102 opened outwardly and provided with inner longitudinal grooves 103. At the other end, body 100 carries the hold flange 105.

Sliding within body 100 of the syringe is a plunger 106 having a thumbpush 107 and disc 25 carrying a rubber gasket 124 abutting against a disc 125 integral with a generally cylindrical fore end 108. Fore end 108 is provided with a cavity 119 and radial cuts 118 allowing the fore end to be opened like a corolla.

The third member of FIG. 1 is a needle 109 integral with a joint or base 110 having outer dimensions corresponding to the inner cavity of projection 102. Base 110 is provided inside with a seat 111 the size of which corresponds to the fore end 108. Formed on the inner walls of seat 111 (FIG. 3) are projections or teeth 112 intended to engage corresponding notches or grooves 113 formed on fore end 108. Seat 111 communicates with needle 109 through a conical projection 114 hanging from socket 115 at the base of needle 109. Socket 115 is provided with tabs 116 radially projecting and facing grooves 103 and projections 104 in spout 102. Projecting tabs 116 and the corresponding projections 104 are three in number but it is evident that this number may be varied.

Figure 3:
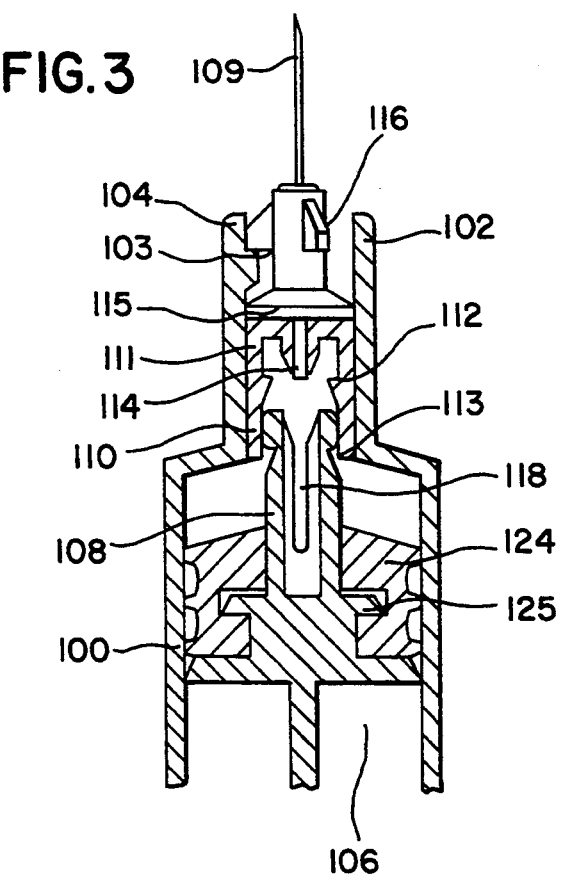
FIG. 3 shows in an enlarged scale the syringe with the extracted needle ready for use and the plunger at the beginning of the filling.

In operation, the syringe appears as in FIG. 3, needle 109 being integral with the body 100 of the syringe, plunger 106 being retracted. This position is reached by first, pushing forward plunger 106 which fore end 108 is already releasably positioned into the base of the needle 109 as shown in FIG. 1, so that the needle can project from fore spout 102 and tabs 116 can slide in grooves 103, whereupon the plunger is rotated clockwise or anticlockwise so that tabs 116 can abut against and be retained by projections 104. In such a position the syringe is ready to be filled by sucking in the substance to be injected, i.e. moving back the plunger easily disengageable from the needle already locked.

During the injection plunger 106 is pushed forward up to the end of the stroke and the conical projection 114 of the needle enters fore end 108 of the plunger and spreads apart the walls thereof so that notches or grooves 113 engage teeth 112 of base 110 of the needle which is now integral with the plunger, thus preventing the syringe to be filled up again. Thereafter the plunger is now rotated anticlockwise or clockwise to disengage tabs 116 from projections 104 so that needle 109 can return within body 100 of the syringe under safety conditions. Now plunger rod 106 can be broken at its predetermined break point designated by 117 in FIG. 2, and needle 109 remain locked in its position inaccessible from the outside.

The outer surface of socket 115 and the inner surface of spout 102 can be knurled to increase the adherence between needle and spout of the syringe.

In FIG. 4, an alternative solution of the above described coupling base between needle and plunger is shown. In FIG. 4 the widening member is suitably shaped to engage a corresponding seat formed in fore end 108.

This invention has been shown and described according to a preferred embodiment but it should be understood that construction modification can be made without parting from the scope of this industrial invention.

I claim:

1. A single-use safety syringe comprising an outer cylindrical body (100) provided with an end spout (102), a needle (109) provided with a joint (110) adapted to releasably engage the inner wall of said end spout, and a plunger (106) provided with a fore end (108) adapted to releasably inwardly engage said joint of the needle so as to allow the plunger to move into the syringe and engage said end spout (102) to make the injection, said joint (110) having an inner seat with a widening means (114) projecting downwardly from a base of said seat and projections (112) extending from walls of said seat, said fore end (108) of said plunger (106) having a conical axial cavity (119) open at a frontal face of fore end (108), longitudinal cuts (118) along its generatrix and external grooves (113) around the fore end (108), the outer dimension of said fore end (108) corresponding to the inner dimension of said inner seat of joint (110) whereby when the plunger (106) is at the end of the injection the widening means (114) enters the cavity (119) and forces walls of said cavity to spread and exert radial pressure against inner walls of said joint (110), grooves (113) engaging projections (112) to lock the needle and plunger together thereby preventing reuse of the needle.

2. The syringe of claim 1, wherein the end spout (102) defines interiorly longitudinal grooves (103) and interiorly circumferential projections (104), and wherein the needle (109) defines radially exterior tabs (116) and coupling of needle (109) with end spout (102) retains needle (109) in an operative position while permitting plunger (106) to be disengaged from needle (109).

3. The syringe of claim 1, wherein an outside surface of joint (110) and an interior surface of end spout (102) are knurled.

4. The syringe of claim 2, wherein an outside surface of joint (110) and an interior surface of end spout (102) are knurled.

* * * * *